(12) United States Patent
Holguin

(10) Patent No.: US 9,775,474 B2
(45) Date of Patent: Oct. 3, 2017

(54) BODY DRYING AND INSPECTION APPARATUS

(71) Applicant: Ernesto Holguin, El Paso, TX (US)

(72) Inventor: Ernesto Holguin, El Paso, TX (US)

( * ) Notice: Subject to any disclaimer, the term of this patent is extended or adjusted under 35 U.S.C. 154(b) by 379 days.

(21) Appl. No.: 14/696,953

(22) Filed: Apr. 27, 2015

(65) Prior Publication Data

US 2016/0100720 A1    Apr. 14, 2016

Related U.S. Application Data

(60) Provisional application No. 61/984,178, filed on Apr. 25, 2014.

(51) Int. Cl.
| | | |
|---|---|---|
| *A47K 10/48* | (2006.01) | |
| *A61B 5/00* | (2006.01) | |
| *A61B 5/145* | (2006.01) | |
| *G01G 19/50* | (2006.01) | |

(52) U.S. Cl.
CPC .............. *A47K 10/48* (2013.01); *A61B 5/004* (2013.01); *A61B 5/0077* (2013.01); *A61B 5/742* (2013.01); *A61B 5/7475* (2013.01); *A61B 5/0002* (2013.01); *A61B 5/14532* (2013.01); *G01G 19/50* (2013.01)

(58) Field of Classification Search
CPC ...... A47K 10/48; A61B 5/0077; A61B 5/742; A61B 5/7475; A61B 5/004; A61B 5/0002; A61B 5/14532; G01G 19/50; F26B 19/00
USPC ..................................................... 34/90, 202
See application file for complete search history.

(56) References Cited

U.S. PATENT DOCUMENTS

| | | | |
|---|---|---|---|
| 3,128,161 A * | 4/1964 | Hudon .................... | A47K 10/48 239/587.4 |
| 3,587,118 A | 6/1971 | Compton | |
| 3,711,958 A * | 1/1973 | Lepage .................. | A47K 10/48 34/239 |
| 4,961,272 A | 10/1990 | Lee | |
| 5,003,705 A | 4/1991 | Lee | |
| 5,099,587 A * | 3/1992 | Jarosch .................. | A47K 10/48 34/202 |
| 6,962,005 B1 | 11/2005 | Khosropour | |
| 7,900,371 B1 | 3/2011 | Bullard | |
| 2010/0266776 A1 | 10/2010 | Cooper | |
| 2011/0137268 A1 | 6/2011 | Thomason | |

* cited by examiner

*Primary Examiner* — Jessica Yuen
(74) *Attorney, Agent, or Firm* — Global Intellectual Property Agency, LLC; Daniel Boudwin

(57) ABSTRACT

A body drying and personal inspection apparatus is provided for air drying and for providing the user with several inspection and data input devices. The apparatus comprises a base platform and an upright member with one or more handles to support the user. A blower assembly forces air through the base platform and through an elongated blower tube handled by the user. Further provided is an inspection camera coupled to the blower tube and a foot camera within the base platform, both used to capture images of the user's body while on the platform. A display and processing system is also provided that allows images to be processed and displayed, for input to be received via a user input device, and optionally for data to be transmitted to a third party over a network. The base platform also provides weight measuring capabilities for measuring the weight of the user thereon.

16 Claims, 2 Drawing Sheets

BODY DRYING AND INSPECTION APPARATUS

CROSS REFERENCE TO RELATED APPLICATION

This application claims the benefit of U.S. Provisional Application No. 61/984,178 filed on Apr. 25, 2014. The above identified patent application is herein incorporated by reference in its entirety to provide continuity of disclosure.

BACKGROUND OF THE INVENTION

Field of the Invention

The present invention relates to a drying and inspection apparatus. More specifically, the present invention provides a general purpose drying tool combined with a system for inspecting the body of a user with a health condition to monitor status and progression of the condition over a period of time. Particularly, the device is well suited for diabetic users and for inspecting various portions of the user's body while standing on the apparatus, and for inputting various physiological measurements into a system for tracking the same. Finally, a system within the apparatus provides for communication of the tracked data to a health care provider over a network.

It is well known that diabetes is a condition that causes several complications and is a condition that must be consistently monitored. Areas of concern include glucose levels in the blood stream, the user's body weight, and the condition of limbs and areas of the body that may be affected by reduced blood flow. Diabetics generally monitor these variables and have frequent visits to their healthcare provider to ensure continued health. The present invention provides an apparatus that assists a user in monitoring various inputs related to diabetes, while also allowing data captured from the user to be sent directly to a healthcare provider over a network. This in turn, may improve health monitoring and reduce required healthcare office visits.

In conjunction with monitoring the user's diabetic condition and health status, the present invention provides a general purpose body dryer for after-shower user. The apparatus comprises a base platform with an upstanding upright member for user support. Within the base platform and extending from the upright member is a pair of drying means. In particular, a blower motor and heater assembly forces air through the base platform and towards the standing user standing thereabove. In conjunction with the base platform, an elongated blower tube is provided that a user can control to direct forced air to various parts of his or her body. The dual blower outlets provide a means to dry a user after a shower or bath.

To monitor the user's diabetic condition, or to monitor a user with a different health condition, a system is provided in conjunction with the apparatus that allows the user to be weighed, for images to be captured of the user's anatomy, and for the user to input various physiological data into the system for tracking and for transmission to a healthcare provider. Specifically, a pair of cameras is provided to capture images of the user's body. Bins are provided for bloodwork to be drawn. And finally, a user input device is provided for a user to interact with a graphic user interface displayed on a display screen when entering various physiological data. These may include glucose levels, the user's body weight, and any other data that can be manually entered after being measured with a third party device (e.g. a glucometer, heart rate monitor, or the like).

Overall the present invention provides several functions for general purpose and for specific monitoring purposes. This background section is intended to illustrate some contemplated uses of the present invention. However, it is not desired to limit the scope of the invention to one specific use or for use in conjunction with one specific medical condition. The present invention provides a general usage drying apparatus and health parameter input system, whereby the parameters may be tracked and optionally sent to a healthcare provider for analysis.

SUMMARY OF THE INVENTION

The following summary is intended solely for the benefit of the reader and is not intended to be limiting in any way. The present invention provides a new body drying and inspection apparatus that can be utilized for drying a user on the apparatus and for collecting data regarding the user using one or more inputs.

It is an object of the present invention to provide a personal drying and inspection apparatus that comprises a base platform that is adapted to support a standing user thereupon, an upright member extending from the base platform, a blower motor assembly with a heating element, and a first and second outlet from the blower motor assembly.

Another object of the present invention is to provide a first and second outlet from the blower motor assembly that comprises air outlets from the base platform and a handheld air tube that a user can direct to various portions of the body while on positioned on the base platform.

Yet another object of the present invention is to provide blower motor controls disposed along the upright member for the standing user to energize and to control the blower motor and heating element of the blower motor assembly.

Another object of the present invention is to provide a personal drying and inspection apparatus that comprises a display screen, a user input device adjacent to the blower motor controls, a body inspection camera connected to the elongated tube, a foot inspection camera disposed within the base platform and directed substantially upwards towards the user, and a processing system adapted to receive signals from the inspection cameras and to transmit the signals to the display screen for visualizing a feed from the body inspection camera.

Another object of the present invention is to provide a processing system that further comprises a processor and a memory, wherein the processing system is adapted to capture still images from the feed of the inspection cameras and to receive physiological data from the user positioned on the base platform via the user input device.

Another object of the present invention is to provide a processing system further comprises a network connectivity device for transmitting and receiving signals over a network, wherein the processing system is further adapted to transmit the still images taken by the inspection cameras and the physiological data collected by the user input device over the network and to a healthcare provider.

Another object of the present invention is to provide a personal drying and inspection apparatus that includes a user weight measuring device within the base platform that is adapted to register a weight of the user when the user is positioned on the base platform.

Another object of the present invention is to provide a personal drying and inspection apparatus with one or more trays or bins disposed along the one or more handles extending from the upright member for supporting various items, including diagnostic tools and medical waste.

Another object of the present invention is to provide a personal drying and inspection apparatus that serves as a general purpose drying apparatus, as well as a device that can be employed to monitor the status of a user's condition through the use of visual images and data input by the user after collecting the data from a third party measurement device (e.g. a glucometer, heart rate monitor, or the like).

Another object of the present invention is to provide a personal drying and inspection apparatus that can connect to a network and to a third party healthcare provider to transmit data to the healthcare provider for tracking and for improved diagnostics between office visits.

Another object of the present invention is to provide a personal drying and inspection apparatus that can receive and track user physiology data locally for tracking performance and overall health.

Another object of the present invention is to provide a personal drying and inspection apparatus that can be deployed in a personal environment (e.g. at home) or in a commercial environment (e.g. a hospital, a healthcare facility, or gym).

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
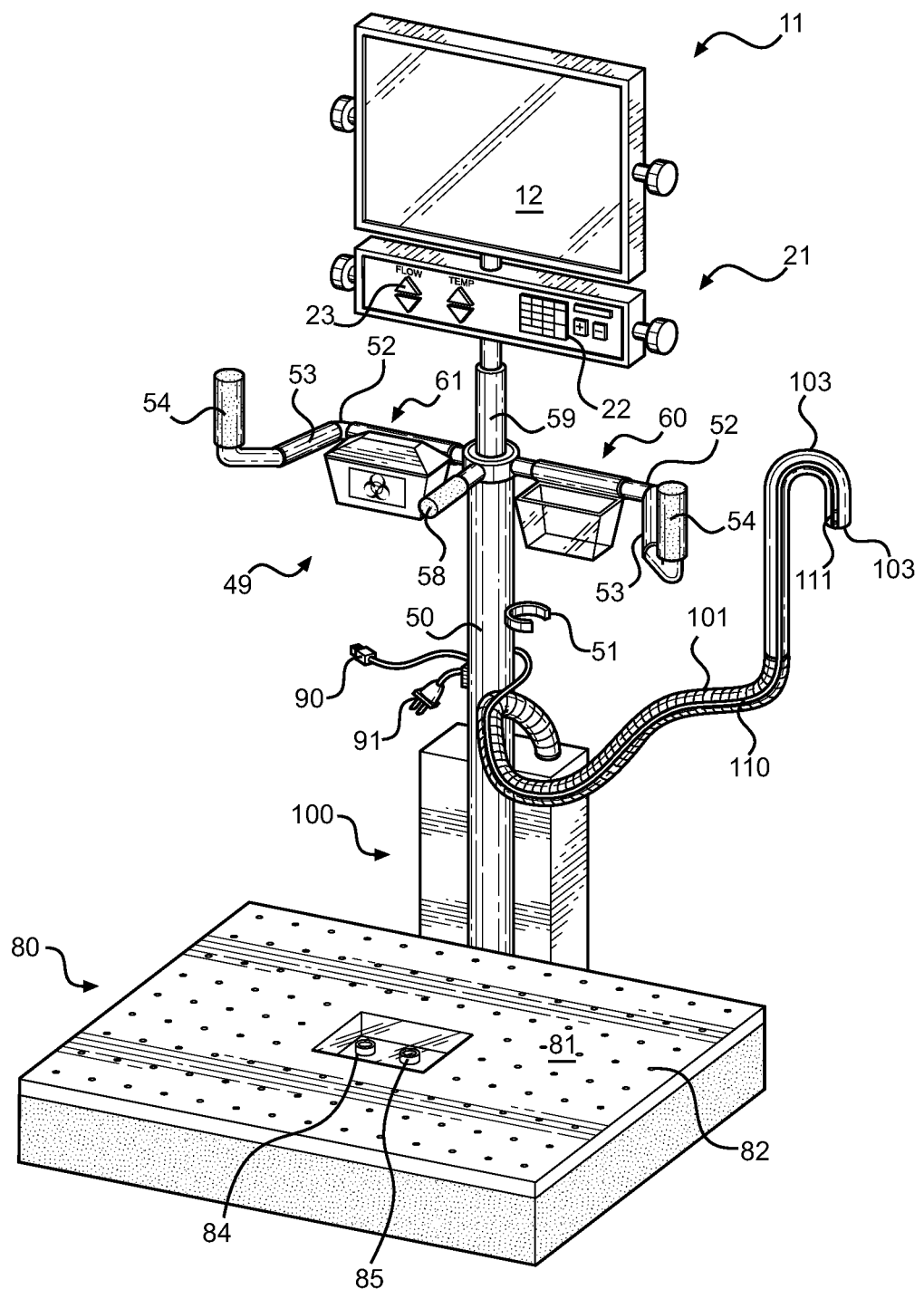
FIG. 1 shows a perspective view of the body drying and inspection apparatus of the present invention.

Reference is made herein to the attached drawings. Like reference numerals are used throughout the drawings to depict like or similar elements of the body drying and inspection apparatus of the present invention. For the purposes of presenting a brief and clear description of the present invention, the preferred embodiment will be discussed as used for drying a user and for measuring, tracking, and transmitting data captured and input into the system to monitor a user's condition and overall health. The figures are intended for representative purposes only and should not be considered to be limiting in any respect.

Referring now to FIG. 1, there is shown a perspective view of the body drying and inspection apparatus of the present invention. The apparatus comprises a base platform 80 that is configured to support a user position thereon, preferably in a standing position but alternatively in a seated position or on a mobility device thereon. The base platform 80 comprises a platform surface 81 upon which the user is positioned while using the apparatus. Extending upwards from the base platform 80 is an upright member 50 that supports one or more handles 49 extending from the upright member. The handles 49 allow the user to grip the same while positioned on the base platform 80 for stability.

When positioned on the base platform 80, the user can engage in several activities, including drying activities, imaging various portions of the user's body, and furthermore entering, viewing, and transmitting physiological data related to the user in the processing system of the apparatus. First, the apparatus functions as a heated, forced air drying device that can dry the user from below and via an elongated air tube 101. Second, a display 11 and input terminal 21 is provided for accessing the system of the apparatus. Finally, an imaging function is provided in the form of a foot camera 85 embedded in the base platform 80 and an inspection camera 101 coupled to the air tube 101.

The drying function of the apparatus is facilitated using a blower motor assembly 100 along the upright member 50, within the base platform, or adjacent to the same. The blower motor assembly 100 comprises an air inlet, a blower motor with an impeller, a power source, and a pair of blower outlets. The blower motor assembly 100 furthermore comprises a heating element such that the forced air from the assembly 100 is heated to improve the drying function of the outgoing air. The user stands or otherwise positions herself onto the base platform 80, whereafter the forced air is used to remove moisture from the user's body after a shower or under other circumstances.

Figure 2:
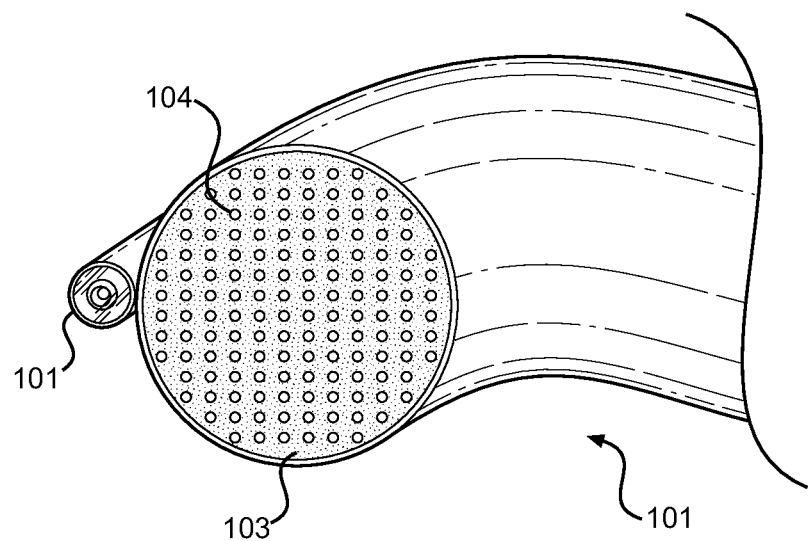
FIG. 2 shows a view of the distal end of the elongated dryer tube that expels forced air and includes an inspection camera for handling by the user.

The first blower outlet from the blower motor assembly 100 comprises an elongated air tube 101 that extends therefrom and allows the user to direct forced air from the blower motor to various portions of the user's body while on the platform 80. The elongated tube 101 includes an elongated, flexible structure that allows positioning of the tube outlet 103 where desired for optimal drying. The distal end of the tube may include a handled portion 103 with a defined curve or a straight length, whereby the user grips the handled portion 103 when operating the tube 101. When stowed, a stowage clip 51 clamps the handle portion 103 against the upright member 50. As shown in FIG. 2, the terminal end 103 of the tube forms the blower outlet, whereby heated forced air is expelled from an open outlet, or alternatively one having an apertured screen surface 104.

The second blower out is disposed within the base platform 80 and comprises a conduit from the blower motor assembly 100 to a plurality of apertures 82 through the upper surface 81 of the base platform 80. The platform apertures 82 allow air to be forced therethrough from the blower motor assembly 100 and from the second blower outlet. The air is directed substantially upwards and onto the user positioned on the base platform 80. This allows for air to move over the user from below while the user engages the tube 101 for more direct drying of other parts of his or her body.

Along the upper end of the upright member 50 is a display 11 and an input device 21 for the user to engage the processing system of the assembly. The processing system is one that takes inputs from the inspection camera 111, the foot camera 84, and the user input device 21 and allows the user to review the input, make updates and inputs, and display the date and/or transmit the data over a network. The processing system may be disposed within the display 11, within the housing of the user input device 21, or alternatively be disposed along the base of the upright member 50. The processing system itself comprises, inter alia, a processor, memory, one or more I/O controllers, a power source, and a network connectivity device. The network connectivity device is a LAN or WAN interface that allows the system to communicate over a wired or wireless network and to communicate with remote servers over the network. Power for the system is preferably provided by a power cord 91 receiving outlet power, while the network connectivity device utilizes either a wireless router or a LAN connector 90 (e.g. an Ethernet cord).

In its inspecting function, the user can engage one or both inspection camera 111, 84 to image different portions of the user's body when on the platform 80. The first inspection camera is a body inspection camera 111 disposed along the length 110 of the tube 101 and terminating adjacent to the distal end 103 thereof. FIG. 2 provides an end view of the elongated air tube 101 and the body inspection camera 101. The body inspection camera 101 is an optical camera that is directed to different portions of the user's body to catalog various problems or conditions (e.g. poor healing skin, rashes, injuries, etc.) that can be captured by the camera. Images, including still and motion images, can be displayed on the screen 12 of the display 11 while the inspection camera 101 is moved around the user's body. Still images can be captured and saved by the processing system for later inspection or for transmission over a network to a third party.

The second inspection camera comprises a foot inspection camera 84 that is disposed within the base platform 80 and directed upwards at the user. The foot inspection camera 84 is used to capture images of a user's foot when placed thereover, which is particularly of interest for diabetics whose limbs suffer from reduced blood flow. The foot camera 84 is embedded within the platform 80 and the user can step thereover for an image of the foot to be taken. An adjacent illumination source 85 may be provided to illuminate the foot when the image is captured.

Figure 3:
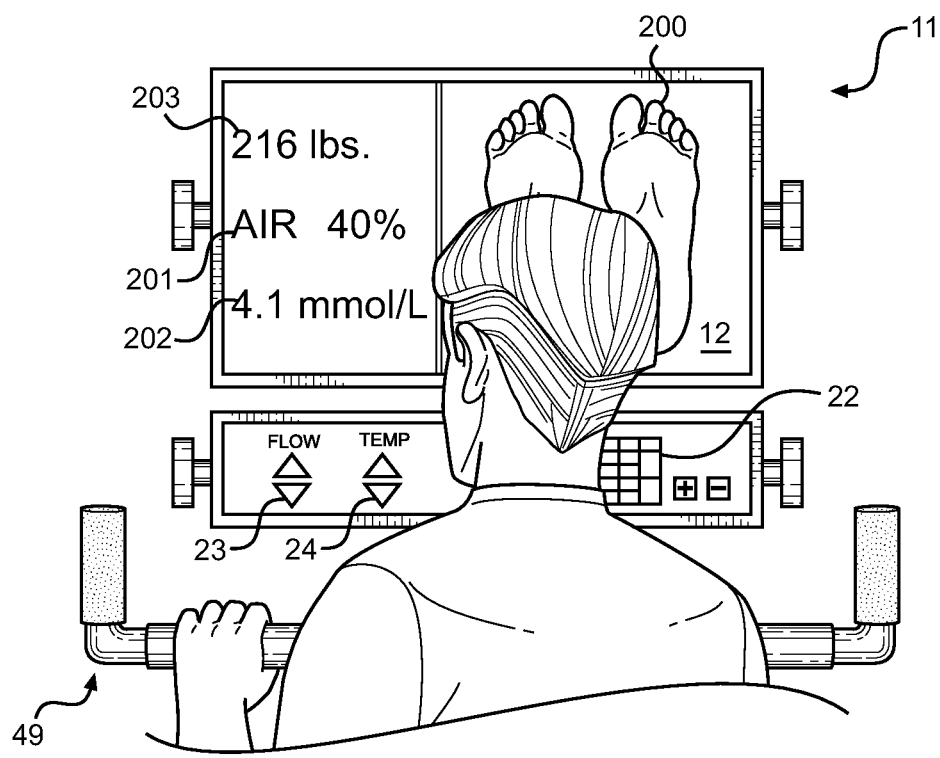
FIG. 3 shows a view of the user inputting date and reviewing imagery on the display device of the present invention.

Each of the cameras is controlled by the user input device 21 along the upper end of the upright member. The user input device 21 and the display device 11, as shown in FIGS. 1 and 3, are used to capture images of the user, to control the operation of the blower motor assembly, and to interface with the processing system via a graphic user interface displayed on the display screen 12. The user input device 21 is an I/O device providing various control buttons 23 and inputs 22 for the user to input alphanumeric data into the system, for controlling the intensity and temperature of the blower motor assembly, for instructing the cameras to capture images, and for navigating the graphic user interface (GUI) of the system. It is not desired to limit the present invention to a specific GUI employed by the system, but rather to provide a multifunction apparatus that provides a body drying device and a body inspecting device in one.

Along the length of the upright member 50 are one or more handles 49. The handles 49 provide user support when standing on the platform 80. The handles 49 may comprise any desired design; however one embodiment contemplates lateral members 52 extending from the sides of the upright member, which connect to upstanding handles 54 via intermediate bars 53. The lateral and intermediate members may support trays 60 and disposal bins 61 that are useful for storage and for disposal of medical waste (e.g. test strips, syringes, etc.). The upper end 59 of the upright member may be telescopically connected thereto and adjustable in height. A height adjuster 58 may be employed to control the vertical height of the upper end 59 and thus the position of the user input device 21 and the display 11.

Referring to FIG. 3, there is shown a view of a standing user interacting with the GUI of the processing system and operating the same. The processing system of the present invention allows the user to capture images using the pair of inspection cameras, while also allowing the user to manually input data into the system. Manually inputted data may include readings or data taken with third party devices, including glucometers, heart rate monitors, or the like. This type of data is manually input so that users can track overall health, track a condition, or send updates to healthcare providers over a network connection. Along with third party devices, the base platform may further include a weight measuring device, such as a scale and sensor to measure the user's weight. The user's weight 203, health data 202, and the imaging data 200 are all inputs into the processing system and can be viewed through the GUI thereof. Moreover, the air blower assembly is controlled by the system, allowing the intensity 201 of the blower motor and the heat therefrom to be controlled to the user's liking.

The data input into the system and the imagery taken by the cameras can be tracked locally by the system and referenced by the user at a later date to track performance. Alternatively, the information can be sent over a network to a third party, such as a healthcare provided operating a system on a remote server. This functions to update a user's healthcare provider between office visits, whereby the healthcare provider can access the information to track the user. This may alert the provider of a worsening or improving condition, may improve the efficiency and effectiveness of office visits, and furthermore reduce the frequency of required visits.

Overall, the present invention provides a new and useful body drying and body inspection device that combines functions of general drying usage with healthcare management. The drawings of the present application are intended to form contemplated embodiments of the apparatus, but should not be deemed limiting to the design of the apparatus. Similarly, the algorithms employed by the processing system and the GUI are representative of the present invention and are also not to be deemed limited to the examples provided in the specification or drawing figures.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A personal drying and inspection apparatus, comprising:
   a base platform which is adapted to support a user positioned thereupon;
   an upright member extending from the base platform;

one or more handles extending from the upright member along its length for the user to grip while positioned on the base platform;

a blower motor assembly comprising a blower motor and a housing, the blower motor assembly having an air inlet and a first blower outlet disposed at the distal end of an elongated tube extending from the blower motor assembly;

the elongated tube extending from the blower motor assembly and being sufficiently flexible for the user to position the first blower outlet towards targeted portions of the user while positioned on the base platform;

a second blower outlet between the blower motor assembly and the base platform;

one or more platform apertures that allow air to be forced therethrough and from the second blower outlet to direct forced air substantially upwards and onto the user positioned on the base platform;

a heating element within the blower motor assembly for heating air forced through the first blower outlet and the second blower outlet;

blower motor controls disposed along the upright member for the user to energize and to control the blower motor and heating element of the blower motor assembly.

2. The personal drying and inspection apparatus of claim 1, further comprising:

a display screen;

a user input device adjacent to the blower motor controls;

a body inspection camera connected to the elongated tube, whereby the body inspection camera comprises a lens disposed adjacent to the first blower outlet of the elongated tube such that the user can direct the lens to different body area while positioned on the base platform;

a processing system adapted to receive signals from the body inspection camera and to transmit the signals to the display screen for visualizing a feed from the body inspection camera.

3. The personal drying and inspection apparatus of claim 2, wherein:

the processing system further comprises a processor and a memory;

wherein the processing system is adapted to capture still images from the feed of the body inspection camera;

wherein the processing system is further adapted to receive physiological data from the user via the user input device.

4. The personal drying and inspection apparatus of claim 3, wherein:

the processing system further comprises a network connectivity device for transmitting and receiving signals over a network; and wherein the processing system is further adapted to transmit the still images and the physiological data over the network.

5. The personal drying and inspection apparatus of claim 2, further comprising:

a user weight measuring device within the base platform that is adapted to register a weight of the user when positioned on the base platform.

6. The personal drying and inspection apparatus of claim 1, further comprising:

a display screen;

a user input device adjacent to the blower motor controls;

a foot inspection camera disposed within the base platform and directed substantially upwards, whereby the foot inspection camera comprises a lens that can capture images of a foot of the user positioned thereover;

a processing system adapted to receive signals from the foot inspection camera and to transmit the signals to the display screen for visualizing a feed from the foot inspection camera.

7. The personal drying and inspection apparatus of claim 6, further comprising an illumination source adjacent to the foot inspection camera.

8. The personal drying and inspection apparatus of claim 6, wherein:

the processing system further comprises a processor and a memory;

wherein the processing system is adapted to capture still images from the feed of the foot inspection camera;

wherein the processing system is further adapted to receive physiological data from the user via the user input device.

9. The personal drying and inspection apparatus of claim 8, wherein:

the processing system further comprises a network connectivity device for transmitting and receiving signals over a network; and wherein the processing system is further adapted to transmit the still images and the physiological data over the network.

10. The personal drying and inspection apparatus of claim 6, further comprising:

a user weight measuring device within the base platform that is adapted to register a weight of the user positioned on the base platform.

11. The personal drying and inspection apparatus of claim 1, further comprising:

one or more trays disposed along the one or more handles extending from the upright member.

12. A personal drying and inspection apparatus, comprising:

a base platform which is adapted to support a user positioned thereupon;

an upright member extending from the base platform;

one or more handles extending from the upright member along its length for the user to grip while positioned on the base platform;

a blower motor assembly comprising a blower motor and a housing, the blower motor assembly having an air inlet and a first blower outlet disposed at the distal end of an elongated tube extending from the blower motor assembly;

the elongated tube extending from the blower motor assembly and being sufficiently flexible for the user to direct the first blower outlet towards targeted portions of the user while positioned on the base platform;

a second blower outlet between the blower motor assembly and the base platform;

one or more platform apertures that allow air to be forced therethrough and from the second blower outlet to direct forced air substantially upwards and onto the user positioned on the base platform;

a heating element within the blower motor assembly for heating air forced through the first blower outlet and the second blower outlet;

blower motor controls disposed along the upright member for the user to energize and to control the blower motor and heating element of the blower motor assembly.

a display screen;

a user input device adjacent to the blower motor controls;

a body inspection camera connected to the elongated tube, whereby the body inspection camera comprises a lens disposed adjacent to the first blower outlet of the elongated tube such that the user can direct the lens to different body area while positioned on the base platform;

a foot inspection camera disposed within the base platform and directed substantially upwards, whereby the foot inspection camera comprises a lens that can capture images of a foot of the user positioned thereover;

a processing system adapted to receive signals from the body inspection camera and the foot inspection camera and to transmit the signals to the display screen for visualizing feeds from the body inspection camera and the foot inspection camera;

wherein the processing system is further adapted to receive physiological data from the user via the user input device.

13. The personal drying and inspection apparatus of claim 12, wherein:

the processing system further comprises a processor and a memory;

wherein the processing system is adapted to capture still images from the feed of the body inspection camera;

the processing system further comprises a network connectivity device for transmitting and receiving signals over a network; and wherein the processing system is further adapted to transmit the still images and the physiological data over the network.

14. The personal drying and inspection apparatus of claim 12, further comprising:

a user weight measuring device within the base platform that is adapted to register a weight of the user when the user is positioned on the base platform.

15. The personal drying and inspection apparatus of claim 12, further comprising an illumination source adjacent to the foot inspection camera.

16. The personal drying and inspection apparatus of claim 12, further comprising:

one or more trays disposed along the one or more handles extending from the upright member.

* * * * *